United States Patent [19]

Langdon

[11] 4,011,389

[45] Mar. 8, 1977

[54] GLYCOSIDE POLYETHERS

[75] Inventor: William K. Langdon, Grosse Ile, Mich.

[73] Assignee: BASF Wyandotte Corporation, Wyandotte, Mich.

[22] Filed: Mar. 21, 1975

[21] Appl. No.: 560,728

[52] U.S. Cl. .................................. 536/4; 162/175; 252/89 R; 252/352; 536/1; 536/120

[51] Int. Cl.² ...................................... C07H 15/04

[58] Field of Search .................. 260/209 R, 210 R; 536/1, 4, 120

[56] References Cited

UNITED STATES PATENTS

| | | | |
|---|---|---|---|
| 3,305,535 | 2/1967 | Merten et al. | 260/209 R |
| 3,510,471 | 5/1970 | Case | 260/209 R |
| 3,542,759 | 11/1970 | Gelotte et al. | 260/209 R |
| 3,640,998 | 2/1972 | Mansfield et al. | 260/210 R |
| 3,737,426 | 6/1973 | Throckmorton et al. | 260/210 R |

*Primary Examiner*—Johnnie R. Brown
*Attorney, Agent, or Firm*—John W. Linkhauer; Bernhard R. Swick; Robert E. Dunn

[57] ABSTRACT

To obtain nonionic surfactants having solubility and stability in relatively strong aqueous solution of caustic, salt or other electrolytes, corn starch or a similar source of glucose units is reacted with an alcohol containing up to about 4 carbon atoms to obtain a glycoside somewhat more lipophilic than the saccharide, and then the resulting glycoside is reacted with a hydrophobic oxirane-containing material such as a $C_6$ to $C_{18}$ epoxyalkane or a glycidyl ether having about the same number of carbon atoms.

7 Claims, No Drawings

GLYCOSIDE POLYETHERS

BACKGROUND OF THE INVENTION

1 Field of the Invention

This invention relates to the chemistry of carbon compounds and, in particular, to derivatives of carbohydrates that comprise modified glycosides. The materials of the instant invention may also be considered as ethers derived from cellulose or ethers derived from starch.

The invention relates moreover, in particular, to nonionic surface-active agents and to biodegradable detergents.

2. Description of the Prior Art

Nonionic surface-active agents made with the use of one or more alkylene oxides are well known. Moreover, nonionic surface-active agents based upon dextrose or another carbohydrate (providing the hydrophilic moiety), reacted with a fatty-acid-based or other similar long-chain material (providing the hydrophobic moiety) are also well known. Although the vast majority of nonionic surfactants known before the present invention can be used in mildly alkaline media, they are usually unsatisfactory for use in alkaline media of some considerable or great strength. In, for example, an aqueous solution containing 5 or more weight percent of an alkali-metal hydroxide, and especially whenever the composition is heated and/or is kept for a period of time, most nonionic surfactants tend to degrade and darken. Moreover, many of the nonionic surfactants have only limited solubility in moderately strong electrolyte solutions.

Although since about 1964, one supplier of nonionic surfactants has marketed a product which has substantially stability and solubility in moderately strong caustic soda solutions, the precise chemical composition of such product and the method for making such product have not been known to the public. Such product has been used in various ways, including incorporating it along with foam-forming agents into a moderately strong aqueous solution of caustic soda to form a foam-type caustic cleaning agent. Such an agent is used by forcing it through a foaming nozzle onto a surface to be cleaned, such as a greasy wall, and then some time later washing the wall with a stream of water. U.S. Pat. No. 3,547,828 is believed to describe a composition somewhat similar to that of the above-mentioned caustic-soluble nonionic surfactant product.

Also belonging to the prior art is U.S. Pat. No. 3,737,426, which teaches that biodegradable nonionic surfactants may be obtained from starch-derived glycosides by reacting a starch first with a number of moles of short-chain epoxyalkane such as ethylene oxide or propylene oxide (5 to 22 moles of such short-chain epoxyalkane per mole of anhydroglucose unit of starch), and then reacting that product with about one to three moles, per anhydroglucose unit, of a long-chain epoxyalkane containing 6 to 18 carbon atoms. The patent teaches that such a nonionic surfactant has one or more "hemiacetal linkages" (more properly, acetal linkages) in place of the usual polyether linkages and it appears that, accordingly, such a "hemiacetal-linked" non-ionic surfactant is considerably more readily degraded by enzymes present in sewage or raw river water, i.e., such a surfactant is considerably more highly biodegradable. Although the patent contains figures that indicate that its composition must have, in water, relatively excellent surfactant properties, it contains nothing that would indicate to a person of ordinary skill in the art that its compositions would be soluble to any appreciable extent in moderately strong solutions of caustic soda or other electrolytes. Most compounds having a polyoxyalkylene structure are notably poor in solubility in such alkali solutions.

Considerably earlier, it had been taught in U.S. Pat. No. 2,407,002 that is was possible to make glycol glucosides and then to react them with alkylene oxides but, in this reference, it was taught that the preferred alkylene oxides are ethylene oxide and propylene oxide; there is nothing to lead a person of ordinary skill in the art to believe that he should disregard the teachings of the patent and use a higher alkylene oxide or similar glycidyl ether to obtain an alkali-soluble nonionic surfactant.

Also in the prior art is U.S. Pat. No. 3,772,269, which teaches the making of a mixture of a higher-alkyl glucoside and a glycol glycoside in a one-step process. The compositions produced in the patent are indicated as having some surfactant properties, as evidenced by foam values, but nothing in the patent indicates to persons of ordinary skill in the art that its compositions have any substantial solubility in caustic soda or other electrolytes.

In the prior-art nonionic surfactants of which I am aware, there has frequently been reliance upon a joining of the hydrophobic part of the molecule to a remaining part of the molecule through an acetal linkage, such that when the linkage is destroyed, the molecule is cleaved into separate parts which are relatively highly hydrophilic and hydrophobic and are thus no longer themselves surface-active to any appreciable extent. Moreover, such acetal linkages are rather readily severed, especially under acidic conditions. Ether linkages are far more stable. The surfactants of the present invention are believed to comprise molecules in which long-chain alkyl epoxides or other oxirane-containing hydrophobes have been caused to add themselves through an ether linkage to one or more of the hydroxyl groups of the ring or the central portion of a glucosyl unit, rather than merely being connected to the glucosyl unit in question through an acetal linkage, and it is thus believed that as a result of this difference in the chemical structure of the nonionic surfactant product, there are obtained with this invention products which have the ability to continue to exhibit surfactant properties despite the use of the surfactant in various media or under various conditions which would cause any surfactant relying upon an acetal linkage between its hydrophobic and hydrophilic parts to discontinue acting as a surfactant. In this regard, the surfactants of this invention present themselves as being distinguishable from those of U.S. Pat. Nos. 3,547,828; 3,772,269; and 3,737,426.

The invention is at the same time, however, able to be distinguished chemically from other ether-linked non-ionic surfactants not containing any glucosyl units, in that these frequently contain chains of ether-linked lower oxyalkylene units and are often characterized by having little or no stability or solubility in moderately strong alkaline media. In this regard, the surfactants of this invention present themselves as being distinguishable from those of U.S. Pat. Nos. 2,677,700; 2,674,619; 2,979,528; and 2,213,477.

SUMMARY OF THE INVENTION

Nonionic surfactants having good solubility in relatively strong aqueous solutions of caustic, salt, or other electrolytes can be made by reacting corn starch or another source of glucose units with an alcohol containing up to 4 carbon atoms to obtain a hydrophobe-compatible glycoside, and then reacting that glycoside with about 0.25 to 1.2 moles, per glucose unit, of an oxirane-containing hydrophobe material, such as a $C_6$ to $C_{18}$ epoxyalkane or a glycidyl ether containing approximately the same number of carbon atoms.

DESCRIPTION OF THE PREFERRED EMBODIMENTS

This invention concerns the making of nonionic surfactants. In particular, it concerns the making of nonionic surfactants which have good stability and/or solubility in certain media such as strong aqueous solutions of caustic soda, caustic potash, sodium chloride, and/or contain acids.

In addition to the properties indicated above, the novel nonionic surfactant materials of the present invention have the advantage that they are not so greatly dependent for their production upon the use of petroleum as most of the nonionic surfactants of the prior art. A considerable proportion of the weight of the product surfactant is derived from a carbohydrate obtainable from a vegetable source, rather than from petroleum hydrocarbons as in the case of the known nonionic surfactants that are based upon the lower alkylene oxides, alone or with alkylated phenols.

The compositions of the nonionic surfactants of this invention are such that they comprise a hydrophilic moiety which is derived from a source of glucose units (dextrose, sucrose, corn starch, corn syrup, cellulose, etc.) and a hydrophobic moiety which is derived from a hydrophobic oxirane-containing material. The hydrophobic oxirane-containing material becomes attached to the hydrophilic moiety through an ether linkage (rather than through an acetal linkage), so that the resulting surfactant is capable of surviving and yielding its desired effects despite the presence of conditions which would cause an acetal-linked surfactant to be cleaved into its respective components and become ineffective.

Prior to the present invention, nonionic surfactants according to the invention have not been made, because it is not possible to obtain directly any satisfactory reaction between, on the one hand, a hydrophobic oxirane-containing material, such as 1,2-epoxydecane or nonylphenol glycidyl ether, and, on the other hand, a hydrophilic material such as glucose or sucrose or a lower oligosaccharide derived from starch or cellulose. The materials are incompatible, forming a two-phase mixture.

In accordance with the invention, the material which provides a source of glucose units is first reacted in a first step with an alcohol containing up to about 4 carbon atoms to obtain a glucoside or glycoside which is somewhat more hydrophobic than the original starting material and thus somewhat more compatible with the oxirane-containing hydrophobe. It has been found that such glucosides or glycosides are compatible with and reactive towards the oxirane-containing hydrophobe materials and will yield surfactant products which are different from those of the prior art, particularly in regard to their stability in certain media in which various prior-art nonionic surfactants have been found unstable.

When glucose (dextrose) is reacted with an alcohol, a glucoside results. It has been known that the alcohols having up to about 4 carbon atoms can be reacted directly with glucose to obtain a glucoside. Such glucosides are not surface-active materials because they lack an adequate hydrophobic moiety. They are, however, somewhat less strongly hydrophilic than the original glucose. It is a part of the prior art that materials having nonionic surfactant properties may be made by producing such glucosides and then reacting them with a higher-alkyl (hydrophobic) alcohol, by an interchange reaction, to obtain a higher-alkyl glucoside such as decyl glucoside. Decyl glucoside, first prepared by another route involving reagents and procedures that are too costly to be used in large-scale commercial production, has been known for years as a substance having nonionic surfactant properties. It has the disadvantage, however, that its hydrophobe moiety is joined to the glucose unit through an acetal linkage, which means that the product is not stable in some media, particularly in acidic ones. This demonstrates that the initial step of reacting glucose with a lower alcohol to form a glycoside which is thus somewhat less hydrophilic and more compatible with a hydrophobe, as a first step in the production therefrom of a nonionic surfactant by subsequent reaction with a hydrophobe incompatible with the initial glucose-source compound, is not novel in itself. Such a procedure is inherent in the practice of the invention of U.S. Pat. No. 3,772,269, and U.S. Pat. No. 3,737,426 provides another example of the use of such an initial glycoside-forming step.

In accordance with the present invention, however, it is found that such a step followed merely by a second-step reaction of the glucoside or glycoside so obtained with an appropriate hydrophobic oxirane-containing material, yields an ether-linked nonionic surfactant. The nature of the initial glycoside-forming step is not especially critical in regard to the $C_1$ and $C_4$ primary or secondary alcohol which is used to form the glycoside. Methanol, ethanol, n-propanol, isopropanol, n-butanol, or sec-butanol may be used. T-butanol is not satisfactory because its hydroxyl hydrogen atom is of an appreciably different nature from the hydroxyl hydrogen atoms of the lower primary and secondary alcohols. Substituted lower alcohols may be used, such as methoxyethanol, ethoxyethanol, methoxymethanol, and ethoxymethanol, and so may the lower alcohols having 2 or 3 hydroxyl groups, such as ethylene glycol and propylene glycol and glycerol.

In the matter of the source of glucose units, the preferred agents are corn starch and corn syrup, because of their ready availability and low cost, but dextrose, sucrose, lactose, and cellulose may similarly be used.

As those familiar with carbohydrate chemistry will appreciate, different reactions often occur simultaneously when an alcohol is heated together with a carbohydrate of the kind mentioned above. Water, alcohols and glycols have the property of reacting with disaccharides and higher saccharides, in a process which may be called hydrolysis, alcoholysis or glycolysis, to produce materials in which the average molecule contains fewer monosaccharide units, and in these processes no water is split out or produced; the water or alcohol or glycol is joined to a glucose unit, yielding the simple sugar or a glucoside or glycoside. At the same time, however, there is a competing reaction whereby saccharides (particularly the monosaccharides and to some extent the disaccharides and other lower saccharides) condense, with the splitting out of water, to form molecules having greater numbers of glucose units per molecule. Moreover, the reaction of a simple saccharide with an alcohol or glycol involves a splitting out of water. Such reactions occur simultaneously to various relative extents, depending upon the reactants selected and the conditions used. By using a considerable excess of alcohol or glycol, lower reaction temperatures, shorter reaction times, and a source of glucose units which is a polysaccharide, one may minimize to a desired extent the dehydration-condensation reaction and favor the reactions whereby glucosides and lower glycosides are formed. The converse is also true. Under nearly anhydrous conditions and with a monosaccharide, high reaction temperature and a smaller proportion of alcohol or glycol, the formation of disaccharides, oligosaccharides, etc., is favored. Materials of greater average molecular weight usually have greater viscosity, a greater tendency to be solid at a given temperature, an in many cases a lower solubility. It is, accordingly, desirable to avoid producing a glycoside material having too great an average number of glucose units per molecule, such as more than 20. In many instances, for the purposes of the invention, desirable results are obtained when the product is essentially a glucoside (a glycoside with one glucose unit per molecule).

The reaction of the first step is conducted in the presence of an acidic catalyst. Any suitable acid catalyst may be used, but ordinarily, sulfuric acid is preferred because of its ready availability and low cost.

Ordinarily, the reaction of the first step may be conducted at relatively modest conditions of temperature and pressure, such as 80° to 150° C. and at atmospheric pressure down to 15 millimeters or less of mercury absolute pressure.

In the first step, the proportions of glucose-supplying compound and diol may be varied to suit requirements. Ordinarily, it is satisfactory to use about one to four moles of diol per mole of glucose or glucose unit. It is usually desirable not to use too great an excess of diol, since it is necessary to remove the diol from the product glucoside by vacuum stripping before proceeding to the second step of the reaction.

Those skilled in the art will appreciate that in instances in which a glucoside is available, such as α-methyl glucoside, it may be used as a starting material to supply glucose units, on the same basis as the product of the first reaction step.

The first-step reaction discussed above is then followed by a second-step reaction, in which the glycoside is reacted with an oxirane-containing hydrophobe material. Such oxirane-containing hydrophobe material may be, for example, a 1,2-epoxyalkane containing 6 to 20 carbon atoms. Examples include decylene oxide, dodecylene oxide, or a mixture of $C_{11}$ to $C_{14}$ oxides. Moreover, hydrophobic glycidyl ethers having about the same number of carbon atoms may be used in place of the epoxyalkanes. It is sometimes convenient to obtain an oxirane-containing hydrophobe material by reacting a hydrophobic alcohol with epichlorohydrin, obtaining a chlorohydrin ether which may, if desired, be reacted with caustic to effect a ring closure and obtain a derived hydrophobic glycidyl ether. In some cases, the chlorohydrin ether itself may be mixed with the glycoside and reacted with it under alkaline conditions; when this is done, the oxirane-containing hydrophobe is, in effect, formed in situ and then reacted with the glycoside.

The hydrophobic alcohol used to form hydrophobic glycidyl ether may be a straight-chain higher alkanol having, for example, 6 to 18 carbon atoms. Alkylated phenols such as nonylphenol, octylphenol, or dodecylphenol may be used. Such higher alcohols also will react with lower alkylene oxides such as propylene oxide, ethylene oxide, and the vic-butylene oxides to form adducts which are themselves capable of being reacted with epihalohydrin to yield halohydrin ethers and glycidyl ethers which are of use with the present invention. The formation of such adducts, by adding one or several moles of one or more of such lower alkylene oxide (whether as a heteric-mixture or in sequence) affords in some cases a reasonably convenient way of modifying to some extent the potency of the hydrophobic nature of the oxirane-containing hydrophobe. For example, if the starting material for the hydrophobe is 1-octadecanol and it is considered somewhat too hydrophobic, preparing an adduct of it with several moles of ethylene oxide will give a material somewhat less highly hydrophobic, and conversely, if the starting material is a little less hydrophobic than is desired, it may be reacted with several moles of propylene oxide and/or butylene oxide to obtain a material with greater hydrophobic effect.

Another possibility in regard to the formation of an oxirane-containing hydrophobe is the use of a material derived from a lower alkanol containing 1 to 6 carbon atoms, reacted with several moles of a lower alkylene oxide to form a hydrophobic adduct which is then reacted with epihalohydrin to form a halohydrin or glycidyl ether. In such material a hydrophobic effect is obtained if a ratio of oxygen/carbon atoms less than 0.4 prevails; in other words, although some ethylene oxide may be used, it is essential to use enough propylene oxide or butylene oxide to ensure that the resulting material is hydrophobic.

Still another possibility is to use a hydrophobic polyoxyalkylene glycol itself, one containing about 6 to 40 oxyalkylene units (usually oxyethylene and oxypropylene units, with enough of the latter to give an oxygen/carbon ratio of less than 0.4 and thus yield the desired hydrophobic effect). Such material is, of course, difunctional. Reaction of it with two moles of epihalohydrin yields a difunctional oxirane-containing hydrophobe. Ordinarily it is preferable, if the oxirane-containing hydrophobe to be used is of this nature, to use glucosides or glycosides containing relatively few glucose units, such as 1 to 4 of such units.

Still another possibility is the use of an alkylphenol (or some oxyalkylene adduct thereof) as the basis of the oxirane-containing hydrophobe material. The alkylphenols having alkyl groups containing 4 to 20 carbon atoms are known to be hydrophobic, and some of them such as octylphenol, nonylphenol and dodecylphenol are used in substantial quantities in the making of other commercially available nonionic surfactants.

The reaction of the second step, i.e., the reaction of the glucoside with the epoxyalkane or glycidyl ether, is catalyzed by basic catalysts. Accordingly, at the conclusion of the first step, it is customary to add to the reaction mixture a sufficient quantity of basic material, such as potassium hydroxide or sodium hydroxide, to neutralize the acid that is present and provide a small quantity of basic material to catalyze the second-step reaction. It is usually not necessary or desirable to remove the salt that is formed by the neutralization of the acid catalyst.

In the second-step reaction, there are usually used about 0.25 to 1.2 moles of higher epoxyalkane or glycidyl ether per monosaccharide unit of the glycoside produced in the first step.

The reaction of the second step is generally conducted under conditions of temperature and pressure that are, on the one hand, sufficient to get a satisfactory rate of reaction and, on the other hand, not so stringent as to cause any appreciable degradation of the product. Ordinarily temperatures such as 80° to 160° C and pressures ranging from the atmospheric down to 2 or 3 millimeters of mercury absolute pressure are employed. The reaction time depends principally upon the temperature employed and to some extent upon the scale of the reaction, and it may range from about 20 minutes to several hours.

The 1,2-epoxyalkane or other oxirane-containing hydrophobe which is reacted with the glycoside produced in the first step is believed to be capable of reacting readily with any of the hydroxyl groups present anywhere within the structure of the glycoside. As a result, it is thought that the product surfactant comprises a mixture of various individual species of compounds, which belong to a genus that may be characterized by the structural formula indicated below, namely:

$$RO-(C_6H_{10}O_5)_n-R^1$$

in which ($C_6H_{10}O_5$) represents a glycosyl unit;

$n$ is an integer from 1 to 20;

R is a radical selected from the group consisting of 2-hydroxypropyl, 2-hydroxyethyl, glyceryl, methyl, ethyl, n-propyl, isopropyl, n-butyl, iso-butyl, methoxyethyl and ethoxyethyl, said R being joined to a glycosyl unit through an acetal linkage;

$R^1$ is selected from the group consisting of
$-OCH_2-CHOH-R^2$, $-OCH_2-CHOH-CH_2OR^3$,

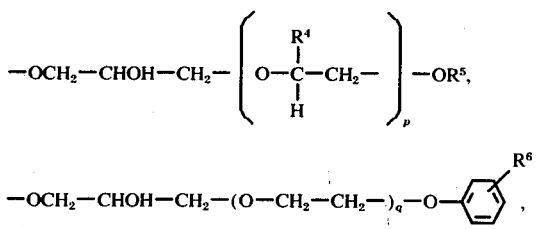

and

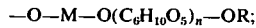
$-O-M-O(C_6H_{10}O_5)_n-OR$;

$R^2$ is an alkyl group containing 6 to 18 carbon atoms;
$R^3$ is an alkyl group containing 6 to 18 carbon atoms;
$R^4$ is selected from the group consisting of methyl and ethyl;
$R^5$ is an alkyl group containing 1 to 6 carbon atoms;
$R^6$ is an alkyl group containing 4 to 20 carbon atoms;
$p$ is an integer of from 3 to 20;
$q$ is an integer of from 0 to 20;
M is a hydrophobic chain of 6 to 40 units selected from the group consisting of oxypropylene and oxypropylene-oxyethylene units wherein the oxypropylene content of said hydrophobic chain is from about 75 to 100 weight percent and the oxyethylene content is from 0 to 25 weight percent; and $R^1$, $R^2$, $R^3$, $R^4$, $R^5$, $R^6$, M, $p$ and $q$ are so selected as to provide that the molecular weight attributable to $R^1$ equals 10 to 80 percent of the molecular weight attributable to the entire molecule.

The foregoing definition embraces a large class of compounds or materials made by reacting a glycoside with an oxirane-containing hydrophobe, and these have in common that they exhibit surfactant properties and are derivable, as to their hydrophile portion, from a non-petroleum source. Moreover, when cornstarch or corn syrup is used as the source of glycosyl units, the hydrophile is relatively inexpensive. Moreover, regardless of the specific nature of the hydrophobe, the nonionic surfactants described above have the hydrophobe joined to the hydrophile through relatively stable ether linkages, which impart stability in acidic media. In the particular cases in which the hydrophobe does not contain any chain of oxyalkylene groups (i.e., the hydrophobe is a $C_8$ to $C_{20}$ 1,2-epoxyalkane, or the glycidyl ether of a $C_6$ to $C_{20}$ alkanol), there is the further property of having appreciable stability and solubility in relatively concentrated aqueous caustic compositions and other electrolytes.

After the second-step reaction has been conducted, the product is packaged in some suitable form for further use and/or storage. In many instances, it is convenient merely to dilute the product to the form of an aqueous solution containing about 20 to 80 weight percent of the product. Alternatively, the product may be poured at high temperature onto a tray or the like and permitted to solidify as a glass or similar composition, which may then be broken into smaller pieces or ground to an appropriate degree of finess, if desired.

The product, made as described above, may be used in various ways that will suggest themselves to persons skilled in the art, such as adding it in small proportions to alkaline cleaning compositions, alkaline electrolytic baths for cleaning or plating metal, alkaline paper-pulp deinking baths, baths for kier boiling of cotton, alkaline baths used in the making of rayon, etc.

The invention is illustrated by the following specific examples.

EXAMPLE 1

To a 1-liter flask, there were added 180 grams of dextrose, 84 grams of propylene glycol, and 0.2 millimeter of concentrated sulfuric acid. The contents of the flask were heated to 115° C, and the mixture became clear, indicating that the dextrose had dissolved. The contents of the flask were then heated to a temperature of approximately 120° C and at an absolute pressure of 150 millimeters of mercury to remove water of reaction. During this operation, the product changed from a clear, light yellow to a clear, dark viscous liquid. After the contents of the flask were cooled to about 100° C, 10 grams of a 20 weight percent solution of potassium hydroxide in methanol were added, and then 94 grams of a mixture of straight-chain $C_{11} - C_{14}$ alkylene oxides, such as that previously sold by Ashland Chemical Company under the name "NEDOX 1114". The mixture was heated to 130° C and maintained at between 130° and 150° C for three hours at atmospheric pressure. Then, unreacted epoxide (61.5 grams) was stripped off by heating the mixture to a temperature of 155° C at an absolute pressure of three millimeters of mercury. There remained a dark-color viscous liquid, which was then dissolved in an equal weight of water to form a 50 weight percent solution.

Good surface-active properties were observed in tests conducted with the material so produced. The 50 percent solution was used to make a 0.1 weight percent solution in water, and the 0.1 percent solution exhibited a Draves sink time (3-gram hook) of 56.4 seconds and a surface tension at 25° C of 32 dynes per centimeter. The Draves sink test, originally described by C. Z. Draves and R. G. Clarkson in volume 20, *American Dyestuff Reporter*, pages 201–208, (1931), has been adopted as Standard Test Method 17–1952, reported in the *Technical Manual* of the American Association of Textile Chemists and Colorists (1964).

Moreover, good solubility in caustic solutions was observed. Two grams of the 50 percent solution dissolved completely in 20 grams of a solution containing 25 weight percent of caustic soda, balance water. Moreover, when 2.0 parts of the above-mentioned 50 percent solution were mixed with 100 parts of the above-mentioned 25 percent aqueous sodium hydroxide solution, the resulting solution had no cloud point, up to 100° C. A mixture of two parts of the 50 percent solution in 100 parts by weight of a 50 weight percent aqueous sodium hydroxide solution was slightly hazy at temperatures between 25 and 99° C, but it had no cloud point.

EXAMPLE 2

To a 1-liter flask, there were added 184 grams of unmodified corn starch containing 12 weight percent of water, 228 grams of methoxyethanol (ethylene glycol monomethylether), and 0.25 milliliter of concentrated sulfuric acid. The flask was equipped with means for maintaining a nitrogen blanket and means for condensing vapors withdrawn from the flask. The flask and its contents were then heated for three hours at atmospheric pressure under a nitrogen blanket at 115° to 128° Centigrade. During this time, the reaction mixture changed from a thick slurry to a fluid light-brown translucent solution, and 69 grams of a distillate were collected.

The distillate was an azeotropic mixture of methoxyethanol with water originally present in the starch. The contents of the flask were then cooled to 55° C and 10 grams of a mixture of 20 weight percent of potasssium hydroxide in methanol were added. Methoxyethanol was removed from material in the flask by distillation at a temperature of approximately 50° to 60° Centigrade and at an absolute pressure that was gradually reduced from 60 millimeters to 25 millimeters of mercury over a 50-minute period. In this way, 133 grams of a further distillate were collected. There were then added to the contents of the flask 94 grams of a mixture of straight-chain $C_{11}$ to $C_{14}$ oxides, such as material previously sold by Ashland Chemical Company under the name NEDOX 1114. The resulting mixture was heated for seven minutes at a temperature of 112° to 130° C and at an absolute pressure of 150 millimeters of mercury to remove the last traces of methoxyethanol, and the reaction mixture was then heated for four hours at atmospheric pressure while the temperature was maintained in the range of 138° to 150° Centigrade. This produced a product, weighing 301 grams, which was poured onto aluminum foil and solidified to a hard, clear, brown glass. This product was partially soluble in 25 weight percent aqueous sodium hydroxide solution. At 0.1 percent concentration in water, it had a Draves sink time (3-gram hook) of 71 seconds and a surface tension of 33.2 dynes per centimeter.

EXAMPLE 3

Following a procedure similar to that outlined in Example 1 above, dextrose was reacted first with propylene glycol, and the resultant hydroxypropylene glycoside was reacted with 1,2-epoxydecane. In place of the 20 weight percent methanolic potassium hydroxide, there was used an equivalent quantity of potassium hydroxide in the form of a fifty weight percent aqueous solution. A solid product was obtained that exhibited, in a 0.1 weight percent solution in water, a surface tension of 31.9 dynes per centimeter and a Draves sink time of 99 seconds. The product was soluble in a 25 weight percent aqueous solution of sodium hydroxide.

EXAMPLE 4

Following a procedure similar to that outlined above in Example 2, starch was reacted with methoxyethanol, and the product was then reacted with a mixture of $C_{14}$ to $C_{16}$ epoxyalkanes. There was obtained a solid product that, in the form of a 0.1 weight percent aqueous solution, gave a surface tension of 29.7 dynes per centimeter and a Draves sink time of 141 seconds.

EXAMPLE 5

A propylene glycol glycoside composition was prepared as follows.

To a 5-liter reaction flask equipped with a stirrer, thermometer, vacuum source, nitrogen source (for blanketing), and a partial take-off distillation head were added 2751 grams of propylene glycol (36 moles) and 1656 grams of Globe corn starch (9 moles) having a moisture content of approximately 12 percent. The flask was blanketed with nitrogen and 10.8 grams of concentrated sulfuric acid were added with stirring. The mixture was heated for approximately two hours at 100 millimeters of mercury pressure while the temperature was gradually raised from 90° C to 124.5° C. During this period, the slurry gradually changed to a nearly clear, pale greenish liquid while 188 grams of condensed volatiles were collected. The volatiles were water contained in the corn starch and a small amount of propylene glycol. Forty-three grams of calcium carbonate powder were added, and the mixture was stirred for 1 hour and 20 minutes. The system was then evacuated to 5–7 millimeters of mercury. Unreacted propylene glycol was removed by distillation over a 4-hour period at a pot temperature of approximately 95° C and a head temperature of 80° C. Propylene glycol (2357 grams) was recovered. The stripped product, weighing 1904 grams, was diluted with 1656 grams of water at a temperature of 94°–100° C. The solution was then treated with 89 grams of decolorizing carbon for 1 hour at 80° C followed by filtration through a sintered-glass funnel with a small amount of diatomaceous earth as filter aid. The 2937 grams of filtrate was treated in a similar manner with carbon a second time. The filtrate, amounting to 2584 grams, was concentrated by distillation at 60–75 millimeters of mercury absolute pressure to 1841 grams. The product was a pale yellow 80 percent solution of propylene glycol glycoside that was used in this form for reaction with glycidyl ethers.

Octyl alcohol was reacted to form a corresponding glycidyl ether as follows.

Octyl alcohol (1436 grams) and boron trifluoride etherate (5 grams) were charged to a 3-liter flask equipped with a stirrer, addition funnel and thermometer. Then, 1221 grams of epichlorohydrin (13.2 moles) were added over a 2-hour period at a temperature of 50°–60° C, and the product, octyl-2-hydroxy-3-chloropropyl ether, was stored at room temperature for further use. The weight was 2672 grams, and the hydroxyl number was 230.

Then, 1446 grams of the above-mentioned octyl-2-hydroxy-3-chloropropyl ether and 723 grams of dimethyl sulfoxide were charged to a three-liter flask equipped with a stirrer and thermometer. The 900 grams of 40 percent sodium hydroxide were added all at once to the flask contents, which were at room temperature. The temperature rose to 48° C over a few minutes. Stirring was continued for approximately 4 hours, during which the temperature fell to 28° C. The product was transferred to a separatory funnel, and the lower aqueous layer was drawn off and discarded. The upper organic layer was washed twice with one-liter portions of water. The following day, the organic layer was transferred to a 3-liter flask and stripped at temperatures up to 90° C and at 3 millimeters of mercury absolute pressure to remove water. The weight of stripped product before distillation was 1208 grams. A 1163-gram aliquot was fractionally distilled, using a 40.6-cm. glass column packed with glass helices, at a pressure of 20–28 millimeters of mercury. Octylglycidyl ether (708 grams) having a boiling point between 132°–135° C at 20 millimeters of mercury was collected. Analysis indicated the oxirane oxygen content as 8.5 percent, versus 8.6 percent theoretical.

The octylglycidyl ether was then reacted with propylene glycol glycoside to yield the desired alkali-soluble nonionic surfactant.

Propylene glycol glycoside (617 grams of 80% solution) octylglycidyl ether (250 grams), both prepared as indicated above, were charged to a flask and stripped under reduced pressure at temperatures of up to 135° C and at 70 millimeters of mercury absolute pressure to remove water in the propylene glycol glycoside. Then, 5 grams of 50 percent sodium hydroxide were added, and water was removed at temperatures of up to 150° C and at 50 millimeters of mercury absolute pressure. Pressure was released to atmospheric pressure with nitrogen, and reaction was conducted for approximately 3 hours at a temperature of 150°–160° C The reaction was exothermic during the first portion of this period. The dark-amber reaction product weighing 747 grams was diluted with 187 grams of water to give an 80 percent solution of surfactant.

When the active surfactant was tested in water at 0.1 percent concentration of the active ingredient, the surface tension was 28.6 dynes, and the sink time as measured by the Draves method was 97.1 seconds. Dynamic foam heights at a flow rate of 400 milliliters per minute at 0.1 percent concentration were 40 millimeters at 25° C and 25 millimeters at 55° C. Details of the Dynamic Foam Test are given in an article by Reich et al. in the April 1961 issue of *Soap and Chemical Specialties*, volume 37, pages 55 et seq. The product had good solubility in an aqueous solution containing 25 weight percent of sodium hydroxide.

EXAMPLE 6

Propylene glycol glycoside was prepared as indicated in Example 5.

A mixture of glycidyl ethers was prepared from a commercially available mixture of octanol (about 45 percent) and decanol (about 55 weight percent). To 1460 grams (10 moles) of such mixture and 5 grams of boron fluoride etherate, there were added 1110 grams (12 moles) of epichlorohydrin over a 2-hour period at a temperature of 38°–60° C. The mixture was stirred for 2 hours at 50°–55° C and then stored at room temperature for further use. The weight of product, an alpha-monochlorohydrin ether mixture, was 2585 grams, and its hydroxyl number was 225.

To 1447 grams of the above-mentioned alpha-monochlorohydrin ether dissolved in 869 grams of dimethyl sulfoxide, there were added 840 grams of 40 percent sodium hydroxide. The temperature rose to 45° C. After stirring for 2 hours, the temperature dropped to 32° C and the reaction mixture was transferred to a 4-liter separatory funnel. One liter of water was added and the layers were separated. The upper layer was washed twice with water and dehydrated under reduced pressure. The weight of product was 1213 grams. A 1146-gram aliquot was fractionally distilled: a mixture of octyl and decyl glycidyl ethers weighing 733 grams and boiling at 108°–150° Centigrade at 6–7 millimeters of mercury was collected.

Then, 100 grams of 80 percent propylene glycol glycoside, prepared as indicated above, and 42 grams of the above-mentioned mixture of octyl and decyl glycidyl ethers were combined in a flask and dehydrated under reduced pressure. One gram of 50 percent NaOH was added, and the mixture was heated up to 140° Centigrade at 400 millimeters of mercury absolute pressure. The mixture was stirred for 3 hours at a temperature between 145°–155° Centigrade. Following this heating period, 2.5 grams of volatiles were removed by vacuum stripping. The product, weighing 118 grams, was diluted with 29.5 grams of water to give an 80 percent solution of surfactant.

At 0.1 percent concentration, the product had a surface tension of 28.3 dynes/centimeter, and a sink time as measured by the Draves method of 112 seconds. The dynamic foam height at a flow rate of 400 milliliters per minute was 90 millimeters at 25° C and 45 millimeters at 65° C. The product also had good solubility in an aqueous solution containing 25 weight percent of sodium hydroxide.

EXAMPLE 7

A propylene glycol glycoside prepared as in Example 5 was reacted with a hydrophobic glycidyl ether based upon oxypropylated n-butanol.

Metallic sodium (8.5 grams) was added to n-butanol (1700 grams) to provide a solution of sodium butoxide catalyst in butanol. An aliquot of such solution (818 grams) was charged to a clean, dry, nitrogen-flushed autoclave having a capacity of about 4 liters. The autoclave was purged at room temperature with nitrogen and pressurized to 2 atmospheres absolute pressure with nitrogen and heated to 115° C. Propylene oxide (1914 grams) was added over a nine-hour period at a maximum pressure of 115 lbs. per square inch gauge while the temperature was maintained at 115° C. Stirring was continued for two additional hours at 115° C, and the contents were discharged after being cooled to 50° C. The weight of the product was 2707 grams. Catalyst was removed from the product by treatment with 81 grams of finely divided synthetic magnesium silicate for one hour at 80° C, followed by filtration. The weight of the filtrate was 2563 grams. Volatiles remaining in the product were then removed by vacuum stripping at 3 millimeters of mercury absolute pressure, while the temperature was raised to 90° C. The weight of the product after removal of volatiles was 2396 grams. Analysis indicated the product to have a hydroxyl number of 219, which corresponds to a molecular weight of 256. This corresponds to an oxypropylated butanol having approximately 3 oxypropyl groups.

The above-mentioned oxypropylated butanol was converted to a corresponding hydrophobic glycidyl ether. To a 2-liter flask equipped with a stirrer, thermometer, and addition funnel, there were added 1280 grams (5 moles) of the above-mentioned oxypropylated butanol and 2.6 grams of boron fluoride etherate catalyst. The contents of the flask were warmed to 50° C, and 555 grams (6 moles) of epichlorohydrin were added from the addition funnel over a period of 1 hour at a temperature of 50° to 59° C. Stirring was continued at 50° to 59° C for 2 hours, and the product was then stored at room temperature without any further treatment. After standing for several days, the product was reacted with caustic soda to form the corresponding glycidyl ether. This was done by placing 1200 grams of a 40 weight percent aqueous solution of sodium hydroxide in a 3-liter flask and warming the contents of the flask to 40° C. Then, the epichlorohydrin adduct, described above, was added to the caustic soda solution with stirring over a period of 30 minutes. The resulting milky slurry was heated to 80° C and stirred for 30 minutes. It was then cooled to 40° C and diluted with 700 grams of water to dissolve the sodium chloride. The organic layer was separated and was stripped of volatiles by being subjected to temperatures up to 100° C at 5 millimeters of mercury absolute pressure. Thereafter, the product was treated with 49.5 grams of synthetic magnesium silicate and filtered to remove any residual base that may have been present. The filtrate was clear, and weighed 1578 grams. Analysis gave an oxirane oxygen content of 4.22 weight percent, a chlorine content of 3.1 weight percent, and a hydroxyl number of 27.8. The product is thus a glycidyl ether according to the invention, having as a major component a compound having a structural formula of

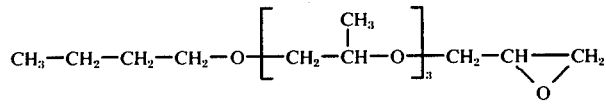

To a 1-liter flask blanketed with nitrogen and equipped with a stirrer, addition funnel, thermometer, and vacuum take-off head, there were added 300 grams of propylene glycol glycoside solution, prepared as indicated in Example 5, and 8 grams of a 50 weight percent aqueous solution of sodium hydroxide. Water was removed by distillation at 5 millimeters or mercury absolute pressure and at temperatures of up to 147° C. Using such conditions, 71 grams of volatiles were taken off, over a period of 38 minutes. Then, 240 grams of the glycidyl ether prepared above were added dropwise at 140° to 149° C over a period of 1 hour. At the start of the reaction, the reaction mixture was highly viscous, and it became readily stirrable as the glycidyl ether was added. After completion of the addition, the reaction mixture was stirred for 1 hour at 140° to 146° Centigrade. The weight of the product was 477 grams. Two hundred grams of the product were diluted with 50 grams of water to give a product containing 80 weight percent of solids. Upon standing such product, two phases formed, which were separated at 90° C. The upper layer comprised 70 weight percent of the product, had a solids content of 80 percent, and contained the above surfactant ingredient. The lower layer, comprising 30 percent of the product, had a solids content of 82 weight percent, and consisted chiefly of unreacted propylene glycol glycoside. Material from the upper layer was then used in tests to determine surfactant properties. A Draves sink test using a 3-gram hook was conducted upon an aqueous solution containing 0.1 weight percent of the active ingredient, the oxypropylated n-butyl glycidyl ether adduct to propylene glycol glycoside, and a wetting-out time of 69 seconds was observed. The same 0.1 weight percent solution exhibited a surface tension of 30.4 dynes per centimeter at 25° C, and no foaming when tested in a Dynamic Foam Test at 400 milliliters per minute at temperatures of 25° and 55° C.

EXAMPLE 8

A different hydrophobic glycidyl ether, based upon butanol plus 6 moles of propylene oxide, was prepared. A 482-gram aliquot of the solution of n-butanol and sodium butoxide described above in Example 7 was charged to a 4-liter autoclave and reacted with 2367 grams of propylene oxide by procedures similar to that used in Example 7. The weight of product discharged from the autoclave was 2801 grams, and the weight after treatment with finely divided magnesium silicate and stripping was 2658 grams. Analysis indicated a hydroxyl number of 132, which corresponds to an average molecular weight of 425 and the structure of an oxypropylated butanol having approximately 6 oxypropyl groups.

Then, 850 grams (2 mole equivalents) of the oxypropylated butanol prepared as indicated above was reacted with 222 grams (2.4 moles) of epichlorohydrin in the presence of 2 grams of boron fluoride etherate as catalyst, by a procedure similar to that described above in Example 7. This yielded a product which was reacted with caustic soda and subsequently treated with synthetic magnesium silicate, as described in Example 7. The weight of the product after filtration was 1041 grams. Analysis gave an oxirane oxygen content of 2.69 weight percent, a chlorine content of 2.5 weight percent, and a hydroxyl number of 29.3. There is thus made a hydrophobic glycidyl ether that may be considered as having as a major component a compound having the structural formula of

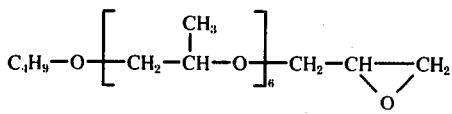

Material so prepared was reacted with propylene glycol glycoside to yield a nonionic material having surfactant properties. This was done as follows.

To a 1-liter flask, there were charged 300 grams of an 80 weight percent aqueous solution of propylene glycol glycoside, prepared as indicated above in Example 5. Stripping at 3 millimeters of mercury absolute pressure and at temperatures of up to 153° C removed 80 grams of volatiles. Then, 240 grams of the material prepared in this example were added over a period of 25 minutes while the reaction mixture was maintained at a temperature between 140° and 150° C. Then, 30 grams of the 50 weight percent aqueous solution of sodium hydroxide were added, and water was removed by stripping at 50 to 60 millimeters of mercury absolute pressure and at temperatures up to 160° C. The reaction mixture was then stirred for 2 hours at 150° to 160° C at atmospheric pressure. The weight of the product was 456.5 grams. A 200-gram portion of the product was diluted with 50 grams of water to give an 80 weight percent concentration. Two layers were formed, which were separated at 90° C. The upper layer comprises 70 weight percent of the product and contained 90.3 weight percent of solids; the lower layer comprised 30 weight percent of the product and contained 67.8 percent of solids. Material from the upper layer was used in tests to evaluate surfactant properties. An aqueous solution containing 0.1 weight percent of active ingredient gave a Draves sink time (3-gram hook) of 26 second and a surface tension of 30.2 dynes per centimeter. In a Dynamic Foam Test at 400 milliliters per minute, the foam height was 5 millimeters at both 25° and 55° C.

EXAMPLE 9

Still another hydrophobic glycidyl ether was prepared, based upon n-butanol and approximately 8 to 11 moles of propylene oxide per mole of butanol. N-butanol (293 grams, 4 moles) containing 1 weight percent of sodium ion was reacted with propylene oxide (2509 grams) in a manner similar to that described in Example 7. The weight of product after treatment with finely divided synthetic magnesium silicate and stripping was 2580 grams. The hydroxyl number was 83, which corresponds to an average molecular weight of 676.

The oxypropylated butanol prepared above (1352 grams, 2 moles) was reacted with 222 grams (2.4 moles) of epichlorohydrin in the presence of 2.8 grams of boron fluoride etherate as catalyst, in a manner similar to that described in Example 7. The weight of product, after stripping and treatment with synthetic magnesium silicate, was 1514 grams. Analysis gave an oxirane oxygen content of 1.76 weight percent, a chlorine content of 1.2 weight percent, and a hydroxyl number of 25.

The glycidyl ether so made was used to prepare a nonionic material having surfactant properties, by reaction with propylene glycol glycoside. An aqueous solution containing 80 weight percent of propylene glycol glycoside, prepared as indicated above in Example 5 (200 grams) was stripped at 5 millimeters of mercury absolute pressure and at temperatures of up to 135° C, to remove water. Then, 100 grams of the glycidyl ether prepared in this example were added, followed by the addition of 6 grams of a 50 weight percent aqueous solution of sodium hydroxide. Stripping was then conducted at 50 millimeters of mercury absolute pressure and a temperature of 140° C. Vacuum was released with nitrogen to atmospheric pressure, and the reaction was continued at 145° to 155° C for two hours. The weight of the product was 256 grams. In surfactant tests at 0.1 weight percent concentration in aqueous solution, the product had a Draves sink time (3-gram hook) of 122 seconds and a surface tension of 30.8 dynes per centimeter.

EXAMPLE 10

An ethylene glycol glycoside was prepared and reacted with 2-ethylhexyl glycidyl ether.

The ethylene glycol glycoside was made as follows. Corn starch (1840 grams, 10 anhydroglucose units) was added to ethylene glycol (2480 grams, 40 moles), 18.8 grams of concentrated sulfuric acid, and 32 grams of a 50 weight percent solution of hypophosphorous acid. The mixture was heated to 120°– 123° C, while the pressure was gradually reduced from atmospheric pressure to 50 millimeters of mercury over 1.5 hours. At this stage, the starch slowly had been transformed into a clear, golden liquid. Barium hydroxide octohydrate (136 grams) was added, and excess glycol was removed by vacuum distillation. To control foaming during this vacuum distillation, a few drops of silicone anti-foaming agent was added. Ethylene glycol (1917 grams) was recovered over a 4.3 hour period, with the final pot temperature being 155° C and the pressure being 4 millimeters of mercury. The weight of the stripped product was 2191 grams. This product was taken up in 1977 grams of water and treated with 95 grams (5 percent by weight) of activated carbon at 80° to 95° Centigrade for 1 hour. The solution was then filtered and concentrated by distillation to 2792 grams. Analysis revealed that the material so prepared had a solids content of 72.6 percent by weight, or 2027 grams. The theoretical yield of ethylene glycol glycoside, assuming that all of the corn starch had been converted to ethylene glycol glucoside, is about 2240; this conversion would require the consumption of 10 moles of ethylene glycol, whereas the amount of ethylene glycol recovered indicates that 9.08 moles of ethylene glycol were consumed. These data indicate that the ethylene glycol glycoside so produced has a high percentage content of ethylene glycol glucoside, probably about 80 to 90 weight percent, and a low content of higher glycoside. The product so made is relatively low in viscosity at temperatures greater than 120° Centigrade.

A hydrophobic glycidyl ether based upon 2-ethylhexanol was prepared as follows. Equimolar portions of 2-ethylhexanol (780 grams) and epichlorohydrin (555 grams) were reacted in the presence of boron trifluoride etherate as catalyst (0.2 percent by weight, based on the alcohol). This yielded a chlorohydrin, which was reacted with a 200 percent stoichiometric excess of sodium hydroxide in the form of a 40 weight percent solution, to prepare the desired glycidyl ether, which was then further purified by distillation, obtaining a product boiling at 127° to 130° C at 20 mm. Hg.

Finally, ethylene glycol glycoside and 2-ethylhexyl glycidyl ether, each as prepared above, were reacted in a weight ratio of 2 parts of glycoside to 1 part of glycidyl ether, in the presence of 1 percent by weight of sodium hydroxide. The sodium hydroxide was added to the ethylene glycol glycoside, and water was removed by stripping at conditions up to 145° C and 5 millimeters of mercury absolute pressure. The glycidyl ether was added over a period of 15 minutes at 140° C, and reacted for 2 hours at 140° to 160° Centigrade. After cooling, water was added to make a solution containing 80 weight percent of solids. The product was soluble in a 25 weight percent aqueous solution of sodium hydroxide to the extent of at least 5 percent by weight. An aqueous solution containing 0.1 weight percent of the active ingredient had a surface tension of 28.7 dynes per centimeter and a Draves sink time of 28.2 seconds.

EXAMPLE 11

Ethylene glycol glycoside is reacted with a diglycidyl ether prepared from a difunctional polyol made by reacting propylene glycol with approximately 12 moles of propylene oxide to obtain a polyol having an average molecular weight of about 775.

In a first step, the above-mentioned polyol is reacted with approximately 2 moles of epichlorohydrin to prepare a dichlorohydrin ether. To a 2-liter five-necked flask provided with a blanket of nitrogen, there are charged the polyol (914 grams or 1.14 moles) and boron trifluoride etherate as catalyst (1.8 grams), and while maintaining a pot temperature at atmospheric pressure of 50° to 68° C, there is added dropwise over a period of approximately one hour epichlorohydrin (232 grams or 2.5 moles). The reaction mixture is permitted to continue to react at pot temperatures ranging from 57° down to 34° C over an additional period of 2 hours and 20 minutes, thereby obtaining a clear, yellowish liquid weighing 1147.8 grams.

In a second step, the dichlorohydrin ether is reacted with sodium hydroxide to effect a ring closure and yield a diglycidyl ether. In a 3-liter flask, 750 grams of an aqueous solution containing 40 weight percent of sodium hydroxide are put at a pot temperature of 25° to 30° Centigrade, and with stirring there are added dropwise over a period of 30 minutes 1142 grams of the above-mentioned yellowish liquid. The reaction is continued at 28° C with fast stirring for 30 minutes, and after the addition of 600 milliliters of tap water and additional stirring for 10 minutes, the contents of the reaction flask are transferred to a 4-liter separatory funnel. There is thus obtained a crude lower-density organic phase weighing 1090 grams, which is filtered to obtain a slightly hazy filtrate weighing 1070.5 grams. Upon being stripped over a period of 50 minutes at conditions ranging from 38° C and 20 millimeters of mercury absolute pressure at the start to 72° C and 2 millimeters of mercury absolute pressure at the end, the filtrate amounts to 1045.5 grams of stripped product (diglycidyl ether).

The stripped product so obtained is then reacted with ethylene glycol glycoside to obtain an alkali-soluble surfactant. To a 500-milliliter four-necked flask provided with a nitrogen blanket, there are charged 137 grams of ethylene glycol glycoside prepared as indicated above in Example 10, and 4 grams of an aqueous solution containing 50 weight percent of sodium hydroxide, and then, over a period of 51 minutes, under conditions ranging from 95° C./450 mm. to 154° C./5 mm. of mercury absolute pressure, the material charged to the reaction flask is stripped, obtaining a take-off of 38.5 grams. The reactor is repressurized with nitrogen to atmospheric pressure, and the temperature of the reaction mixture is raised to 164° C. Then, over a period of 33 minutes, there are added 100 grams of the stripped product (diglycidyl ether) prepared above. The reaction mixture was maintained under reaction conditions, approximately 165° to 190° Centigrade at atmospheric pressure under a blanket of nitrogen with appropriate stirring, for a total period of approximately 10 hours and 22 minutes, obtaining as a product a dark-amber viscous product weighing 201.5 grams, said product being diluted with 50 grams of distilled water admitted to a feed funnel to material, as aforesaid, under a nitrogen blanket, to obtain a product weighing 251.5 grams and containing approximately 80 weight percent of solids.

Such material was used to prepare aqueous solutions containing 1.0 and 0.1 weight percent of active ingredient (solids in product mentioned above). An aqueous solution containing 1.0 weight percent of active ingredient (solids of material prepared above) is found to have a cloud point (not sharp) of 28° C. An aqueous solution containing 0.1 weight percent of active ingredient exhibits a surface tension of 33.5 dynes per centimeter and a Draves sink time (3-gram hook) of 56.4 seconds.

EXAMPLE 12

The glycidyl ether of 2-ethylhexanol was reacted with alpha-methylglucoside to obtain a surfactant.

To a 500-milliliter 4-necked flask, there were charged 150 grams (0.77 mole) of alpha-methylglucoside and 75 grams of 2-ethylhexyl glycidyl ether. The resultant blend was gently heated, using a heat lamp, up to 150° C under a blanket of nitrogen at atmospheric pressure, thereby obtaining a stirrable white slurry. Then, with continuous stirring, the reactor was cooled slightly to 140° C and there were added 1.5 grams of a 50 weight percent aqueous solution of sodium hydroxide as catalyst, and a gentle vacuum (100 millimeters of mercury absolute pressure) was applied to the reactor. Over a period of 24 minutes and a temperature of 130° to 159° Centigrade, 6 grams of volatile matter were recovered. The reactor was then repressurized with nitrogen to atmospheric pressure, and stirring was continued at pot temperatures ranging from 159° to 176° Centigrade for a period of 19 minutes, during which time the initial two-phase material in the reactor turned first medium amber and then completely clear. The material in the reactor was stirred for an additional 27 minutes at 176° to 178° C, then cooled to 100° C and mixed with 55 grams of distilled water to obtain 275 grams of an aqueous solution containing 80 weight percent of active ingredient.

Such aqueous solution was used to prepare an aqueous solution containing 1 weight percent of active ingredient. Such 1% solution had a pH of 6.65 and was milky or cloudy at room temperature.

A solution containing 0.1 weight percent of the active ingredient was prepared. It was milkish and hazy at room temperature and exhibited surfactant properties (Draves sink time, 3-gram hook) of 104.2 seconds and a surface tension of 26.4 dynes per centimeter.

The 80% concentrate was soluble to the extent of at least 5 weight percent in 25 weight percent aqueous caustic soda.

EXAMPLE 13

Ethanol is reacted with glucose in an acidic medium to form an ethyl glycoside. Separately nonylphenol (one mole) is reacted with three moles of ethylene oxide to form an oxyethylated adduct of nonylphenol, which is then reacted first with epichlorohydrin and then with caustic soda to form a glycidyl ether of oxyethylated nonylphenol. The glycoside so formed is reacted with the glycidyl ether under alkaline anhydrous conditions to form a nonionic surfactant.

While I have shown and described herein certain embodiments of my invention, I intend to cover as well any change or modification therein which may be made without departing from its spirit and scope.

We claim:

1. A material having the formula $$RO-(C_6H_{10}O_5)_n-R^1$$

in which $(C_6H_{10}O_5)$ represents a glycosyl unit;

$n$ is an integer from 1 to 20;

R is selected from the group consisting of 2-hydroxypropyl, 2-hydroxyethyl, glyceryl, methyl, ethyl, n-propyl, isopropyl, n-butyl, sec-butyl, methoxyethyl, and ethoxyethyl, said R being joined to a glycosyl unit through an acetal linkage;

$R^1$ is selected from the group consisting of $-OCH_2-CHOH-R^2$, $-OCH_2-CHOH-CH_2OR_3$,

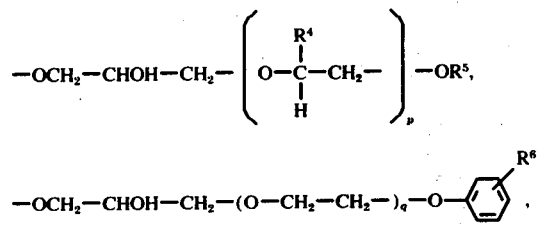

and $-O-M-O-(C_6H_{10}O_5)_n-OR$;

$R^2$ is an alkyl group containing 6 to 18 carbon atoms;
$R^3$ is an alkyl group containing 6 to 18 carbon atoms;
$R^4$ is selected from the group consisting of methyl and ethyl;
$R^5$ is an alkyl group containing 1 to 6 carbon atoms;
$R^6$ is an alkyl group containing 4 to 20 carbon atoms;
$p$ is an integer of from 3 to 20;
$q$ is an integer of from 0 to 20;
M is a hydrophobic chain of 6 to 40 units selected from the group consisting of oxypropylene and oxypropylene-oxyethylene units wherein the oxypropylene content of said hydrophobic chain is from about 75 to 100 weight percent and the oxyethylene content is from 0 to 25 weight percent; and $R^1$, $R^2$, $R^3$, $R^4$, $R^5$, $R^6$, M, p and q are so selected as to provide that the molecular weight attributable to $R^1$ equals 10 to 80 percent of the molecular weight attributable to the entire molecule.

2. A material according to claim 1, wherein $R^1$ is selected from the group consisting of $-OCH_2-CHOH-R^2$ and $-OCH_2-CHOH-CH_2OR^3$.

$R^2$ is an alkyl group containing 6 to 18 carbon atoms; and
$R^3$ is an alkyl group containing 6 to 18 carbon atoms.

3. A material according to claim 1, where R is 2-hydroxypropyl.

4. A material according to claim 1, where R is 2-hydroxyethyl.

5. A materia according to claim 1, where R is glyceryl.

6. A material according to claim 1, where R is a lower alkyl radical containing 1 to 4 carbon atoms, said alkyl radical being a remainder of a non-tertiary alcohol.

7. A material according to claim 1, where $R^1$ is

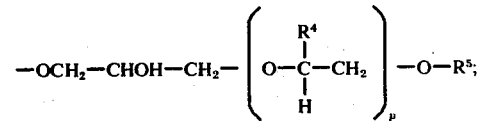

$R^4$ is selected from the group consisting of methyl and ethyl;
$R^5$ is an alkyl group containing 1 to 6 carbon atoms; and $p$ is an integer of from 3 to 20.

* * * * *